United States Patent [19]

Swendson et al.

[11] Patent Number: 4,759,378

[45] Date of Patent: Jul. 26, 1988

[54] FLEXIBLE TIP CARDIAC PACING CATHETER

[75] Inventors: David L. Swendson, Garden Grove; Edward E. Elson, Anaheim; Clement Lieber, Yorba Linda; Michael D. Rold, Costa Mesa, all of Calif.

[73] Assignee: American Hospital Supply Corporation, Evanston, Ill.

[21] Appl. No.: 844,213

[22] Filed: Mar. 18, 1986

Related U.S. Application Data

[63] Continuation of Ser. No. 434,318, Oct. 14, 1982, abandoned.

[51] Int. Cl.⁴ .............................................. A61N 1/04
[52] U.S. Cl. .................................. 128/786; 128/419 P
[58] Field of Search ...................... 128/419 P, 784–788

[56] References Cited

U.S. PATENT DOCUMENTS

| | | | |
|---|---|---|---|
| 3,416,533 | 12/1968 | Fisher et al. | 128/419 P |
| 3,568,660 | 3/1971 | Crites et al. | 128/419 P |
| 3,664,347 | 5/1972 | Harmjanz | 128/419 P |
| 3,788,329 | 1/1974 | Friedman | 128/419 P |
| 3,865,118 | 2/1975 | Bures | 128/786 |
| 3,995,623 | 12/1976 | Blake et al. | 128/419 P |
| 4,080,706 | 3/1978 | Heilman et al. | 128/772 |
| 4,135,518 | 1/1979 | Dutcher | 128/419 P |
| 4,198,991 | 4/1980 | Harris | 128/419 P |
| 4,287,896 | 12/1976 | Grigorev et al. | 128/419 P |
| 4,332,259 | 6/1982 | McCorkle, Jr. | 128/419 P |

FOREIGN PATENT DOCUMENTS 1304231  1/1973  United Kingdom.

OTHER PUBLICATIONS

Diagnostic and Intervention Products for the Radiologist, Cardiologist and Surgeon, Cook Incorporated, Catalog 1978–1980, pp. 46 and 47.

Primary Examiner—William E. Kamm
Attorney, Agent, or Firm—Gordon L. Peterson

[57] ABSTRACT

A flexible tip catheter for electrically stimulating the heart comprising an elongated body having an elongated passage therein and an elongated conductor partially in the passage. The elongated conductor has a distal end portion outside of the passage which is flexible and resilient along its length. The distal end portion includes a flexible resilient electrode exposed at the outer periphery of the catheter so that current can be passed along the conductor to the electrode to electrically stimulate the heart. The distal end portion is more flexible at distal locations than at proximal locations along its length. The flexibility of the distal end portion and of the electrode greatly reduces the risk of penetration of the heart wall.

24 Claims, 2 Drawing Sheets

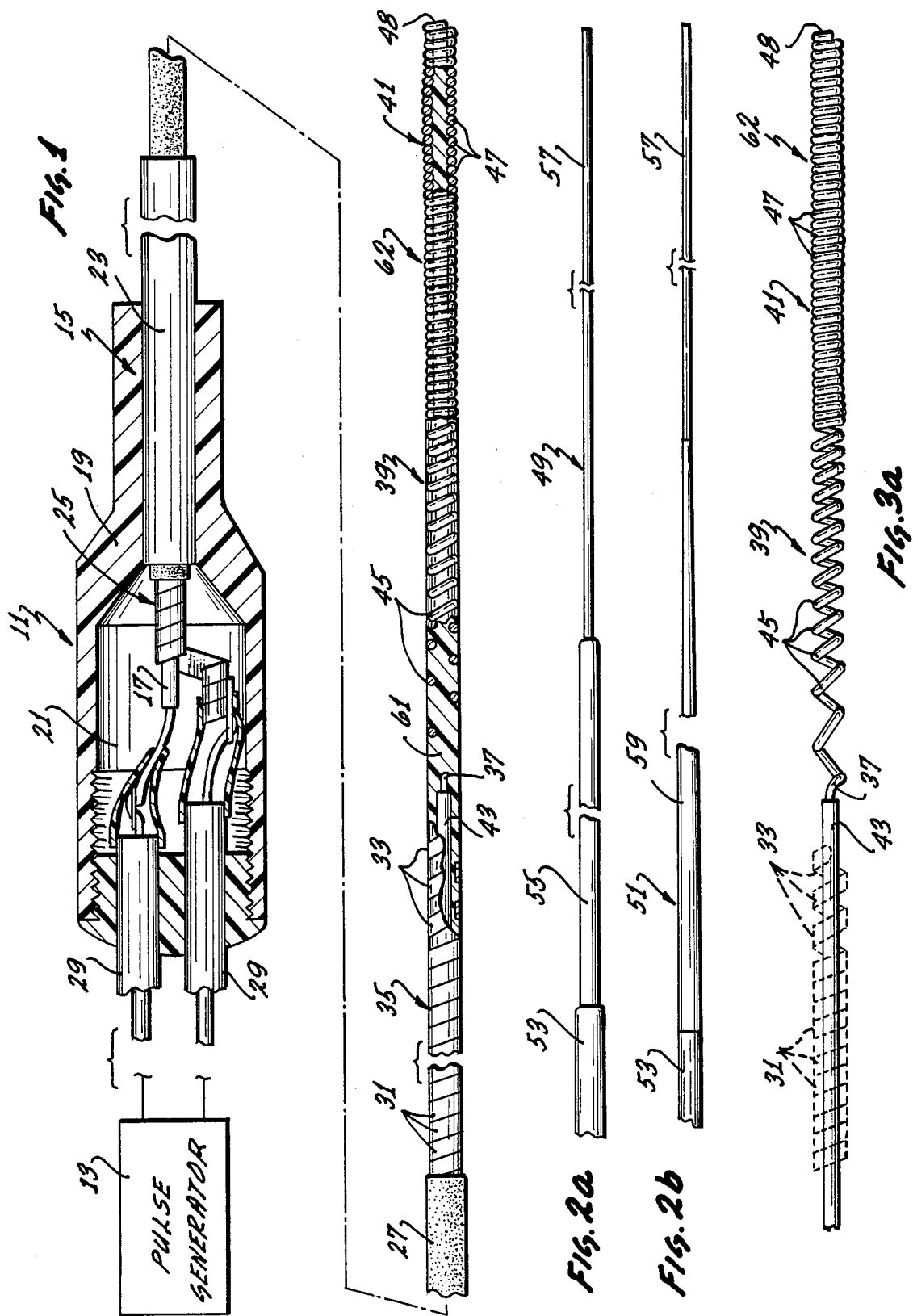

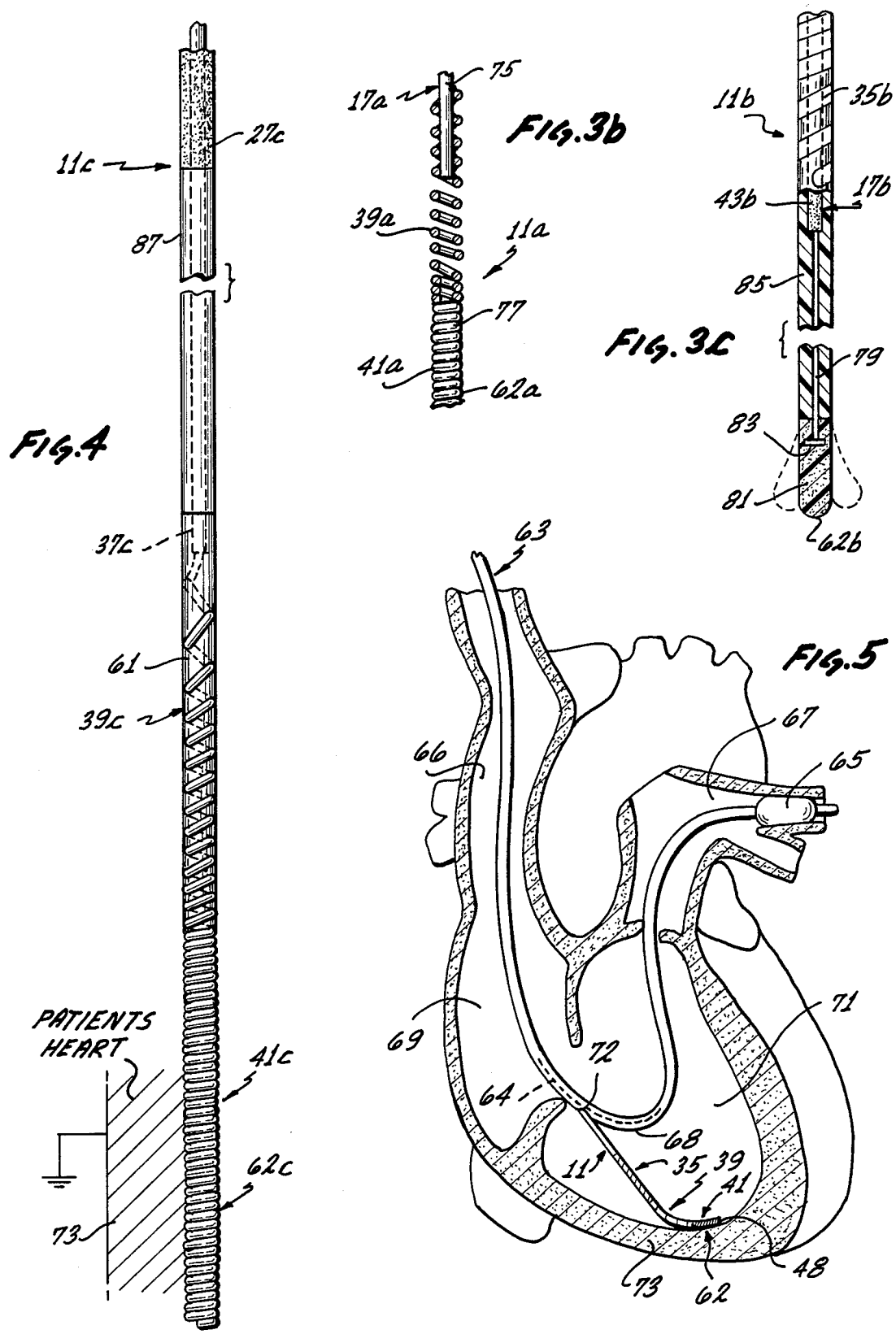

FLEXIBLE TIP CARDIAC PACING CATHETER

This application is a continuation of application Ser. No. 434,318 filed Oct. 14, 1982 and now abandoned, entitled Flexible Tip Cardiac Pacing Catheter.

BACKGROUND OF THE INVENTION

A pacing catheter and a pulse generator are used to electrically stimulate or pace the heart. To accomplish this, the catheter is inserted through a vein into the heart. Typically, the catheter is inserted into the right ventricle. The catheter may be either unipolar, i.e., have one electrode, or bipolar, i.e., have two electrodes. In either event, the distal electrode of the catheter must be brought into contact with the heart wall in order that pulses of electrical energy can be transmitted from the pulse generator through the catheter to the heart. Pacing of the heart in this fashion is often temporary and may be required, for example, in surgery following a myocardial infarction.

One problem with pacing catheters is that the insertion of the catheter through the heart and into engagement with the heart wall creates a risk of penetration of the heart wall by the catheter. The risk of penetration cannot be avoided by making the catheter uniformly flimsy because the catheter must have enough stiffness to be inserted into the heart. In addition, the catheter must have some resilience so that it can maintain the electrodes in substantially continuous contact with the heart wall in the presence of factors such as the beating of the heart and patient movement, which tend to interrupt engagement between the electrodes and the heart wall.

It is known to provide a flexible tail on a heart stimulation catheter and to space the electrodes proximally from the tail as shown in Harmjanz U.S. Pat. No. 3,664,347. In this construction, the tail must be in an artery of the lungs and neither of the electrodes is at or near the distal end of the catheter.

One way to insert a cardiac pacing catheter is to advance it through the lumen of a guiding catheter. To accomplish this, the guiding catheter must first be inserted through a vein and the right heart to the pulmonary artery, and this requires that the guiding catheter be formed into a curve, which is essentially a 180-degree curve in the right heart ventricle. The guiding catheter has a port within or adjacent the curve through which the pacing catheter can extend. One problem with this composite guiding catheter-pacing catheter system is that the guiding catheter tends to form a sharp reverse bend or kink immediately distally of the port, and this is undesirable in that the kink can close off the lumens in the catheter.

SUMMARY OF THE INVENTION

This invention overcomes the pacing catheter insertion problem described above by providing a catheter with a flexible, resilient distal end portion and a flexible electrode. The distal end portion of the catheter has insufficient column strength to perforate the heart wall when the distal end portion is axially pushed against the heart wall. When the distal end portion contacts the heart wall, it bends or deflects and guides the distal end along the heart wall rather than through it. Also, in this bent-over condition, a larger surface area of the distal end portion engages the heart wall thereby decreasing unit loading and making heart wall perforation much less likely to occur.

With this invention, the resilient, flexible characteristic of the distal end portion extends all the way to the distal end of the catheter. This is true even if an electrode of the catheter is at the distal end.

The catheter of this invention can advantageously include an elongated body having an elongated passage therein and an elongated conductor partially in the passage. The elongated conductor has a distal end portion outside of the passage which is flexible and resilient along its length. The distal end portion terminates substantially at a distal end of the catheter. The flexible, resilient distal end portion includes a flexible electrode exposed at the outer periphery of the catheter so that current can be passed along the conductor to the electrode to electrically stimulate the heart. The distal end portion is preferably more flexible closely adjacent the distal end of the catheter than at a location spaced proximately from the distal end of the catheter. More specifically, the conductor may include a first section lying partially within the body, a distal section and a transition section joining the first section to the distal section with each of such sections being more flexible than the section located immediately proximally of such section.

In a preferred implementation, the conductor includes an elongated wire with a distal section and a transition section of the conductor being wound into a coil with the coils of the transition section being spaced greater axially than the spacing between the coils of the distal section. This provides the transition section with greater rigidity and less flexibility than the distal section. Alternatively, or in addition thereto, to enhance flexibility of the wire at distal locations, the cross-sectional area of the wire can be progressively reduced as the wire extends distally. The first section of the wire may be uncoiled The transition section is, therefore, a stiffness transition zone between the relatively stiff first section and the relatively flexible distal section. This transition zone prevents high stress points between the relatively stiff and relatively flexible sections. Without this transition section, permanent deformation is more likely to occur and its fatigue strength reduced.

The features of this invention are applicable to a unipolar or bipolar catheter. In one preferred form of bipolar catheter, the body includes a conductive wire having a plurality of coils with a region of the coils being exposed to define a second electrode. Preferably this wire is rectangular in cross section to increase the stiffness of the body and reduce its electrical resistance.

If desired, the interior of the coils can be filled with an elastomeric material to aid in controlling the flexibility of the distal end portion of the catheter. Also, the elastomeric material can extend beyond the distal tip of the coils to provide a soft distal end to the catheter. Filling of the interior of the coils also prevents the ingrowth of tissue into the coils. Finally, in a bipolar catheter, the elastomer can provide insulation between the two conductors, and by axially spacing coils of the spring forming the second electrode, the elastomer can be provided between the spaced coils to tend to lock the structure together.

The concepts of this invention are not limited to the use of a conductor wound into coils. For example, the conductor may include a body of conductive elastomeric material at the distal end of the catheter. The elastomeric material is soft, flexible and resilient so that it can at least partially define a flexible, resilient distal electrode which performs much like the distal electrode formed by the flexible, resilient coil spring as described above.

The flexible tip catheter of this invention can be inserted without any guiding implement through a vein into the heart. Alternatively, the catheter can be advanced through the lumen of an indwelling right heart monitoring catheter and exit at a side port in either the ventricle or atrium to perform its functions.

This invention also provides a guiding catheter which readily forms into a gentle bend or curve in heart and does not kink when used with a pacing catheter. One reason that a composite catheter system tends to kink is that the catheter system proximally of the port out of which the pacing catheter emerges is relatively stiff, and the guiding catheter distally of the port is relatively flexible. This abrupt change in stiffness at the port tends to cause kinking of the guiding catheter.

With this invention, a stiffening element, such as an elongated polymeric or metallic wire, is permanently fixed, as by bonding, within the guiding catheter. The stiffening element begins proximally of the port and extends to a location distally of the port so that the region through the port and distally thereof is stiffened. The degree of stiffening is such as to permit the guiding catheter to form into the desired gentle curve without kinking. Preferably, the stiffening element terminates no farther distally than the right ventrical and no farther proximally than the superior vena cava. When the catheter system is used for pacing the right ventrical, the stiffening element preferably terminates at its opposite ends in the right atrium and the right ventricle.

The guiding catheter and the pacing catheter of this invention can be used separately or in combination. Also, the guiding catheter can be used with other pacing catheters, and the pacing catheter of this invention can be used with other guiding catheters.

The invention, together with additional features and advantages thereof, may best be understood by reference to the following description taken in connection with the accompanying illustrative drawing.

BRIEF DESCRIPTION OF THE DRAWING

FIG. 1 is a side elevational view partially in section of a bipolar catheter constructed in accordance with the teachings of this invention coupled to a pulse generator.

FIGS. 2a and 2b are fragmentary side elevational views showing two different forms of wire which can be used for the conductor.

FIGS. 3a, 3b and 3c are side elevational views of three forms of bipolar flexible tip catheters of this invention, respectively. The elastomeric material within the coils is not shown in FIGS. 3a and 3b.

FIG. 4 is a front elevational view of a unipolar catheter constructed in accordance with the teachings of this invention.

FIG. 5 is a sectional view through a human heart showing one way in which the catheter of this invention can be used.

DESCRIPTION OF THE PREFERRED EMBODIMENTS

FIG. 1 shows a bipolar catheter 11 electrically coupled to a pulse generator 13. Generally, the catheter 11 comprises a body 15 and an elongated inner conductor 17.

The body 15 includes a backshell 19 having an interior chamber 21, a tube 23 received within one end of the backshell 19, an outer conductor 25 and a flexible outer cover 27 of a suitable material, such as polytetrafluoroethylene. The conductors 17 and 25 are suitably coupled within the chamber 21 to leads 29 leading to the pulse generator 13. The chamber 21 may contain a suitable potting compound (not shown) if desired.

In the embodiment illustrated, the outer conductor 25 is in the form of a flat wire, i.e., a wire of nearly rectangular cross section, wound into a series of contiguous coils 31 which extend from the chamber 21 to a location distally of the cover 27 and axially spaced coils 33 located distally of the contiguous coils 31. The cover 27 terminates proximally of the distal end of the conductor 25, and the exposed portion of this conductor forms an electrode 35.

The inner conductor 17 is also in the form of an elongated wire having a first section 37 extending from the chamber 21 axially through the body 15, a transition section 39 and a distal section 41 with the portion of the inner conductor 17 which is outside of said body being the distal end portion of the inner conductor. As best shown in FIG. 3a, the first section 37 is straight and is covered by insulation 43. The transition section 39 comprises a plurality of coils 45 which is spaced apart axially, with the axial spacing between adjacent coils progressively reducing as the transition section extends distally. This progressive reduction in spacing is preferred but not essential. The distal section 41 comprises a plurality of contiguous coils 47 and terminates at a distal end 48 of the catheter 11. These coils could be tightly or loosely wound to further control flexibility.

The inner conductor 17 may be formed, for example, of a wire 49 (FIG. 2a) or of a wire 51 (FIG. 2b). The wire 49 has a cylindrical section 53 of relatively large diameter which can be used to form the first section 37 and cylindrical sections 55 and 57 which can be used to form the transition section 39 and the distal section 41, respectively. Each of the sections 55 and 57 is of lesser diameter than the cylindrical section immediately proximally thereof.

The wire 51 also has a cylindrical section 53 from which the first section 37 can be formed. However, in lieu of the cylindrical section 55, the wire 53 has a conical section 59 which is of progressively reducing diameter as it extends distally and from which the transition section 39 can be constructed. The wire 53 also has a cylindrical section 57 from which the distal section 41 can be constructed. The wires 49 and 51 can be constructed of various suitable materials, such as stainless steel. The wires 49 and 51 can be formed of multiple sections which are suitably joined together as by soldering or welding but, preferably, each of these wires is integral. In this latter event, the wire 51 can be tapered by electropolishing or centerless grinding.

With the construction described above, the first section 37 is less flexible than the transition section 39 and the transition section 39 is less flexible than the distal section 41. Also, the first section 37 is reinforced by the body 15. Moreover, the flexibility of the transition section 39 increases as the transition section extends distally. The relative stiffness of the first section 37 is obtained by leaving the first section 37 uncoiled and constructing it of larger diameter wire. The transition section 39 is more flexible than the first section 37 because it is coiled and constructed of smaller diameter wire. The flexibility of the transition section 39 increases because the axial spacing between the coils 45 decreases as the transition section extends distally and because the conical section 59 of the wire is of progressively decreasing diameter. The distal section 41 is more flexible than the transition section 39 because the coils 47 are contiguous and because wire of minimum diameter is used to construct it. The distal section 41 is flexible and resilient all the way to the distal end 48.

In the embodiment of FIGS. 1-3a, a non-conductive elastomer 61 fills the central space within the coils 47, 45 and 33. The elastomer 61 helps insulate the conductors 17 and 25 from each other. In the embodiment illustrated, the elastomer 61 terminates, along with the distal section 41, at the distal end 48. In this embodiment, the presence of the elastomer 61 does not alter the above-described relative stiffness relationships of the sections 37, 39 and 41. The elastomer 61 fills the spaces between the coils 45 and the coils 33, and in addition, encases the coils 45 of the transition section 39 so that only the coils 47 are exposed to define an electrode 62. In this embodiment, the distal section 41 forms the electrode 62. If the elastomer 61 is eliminated, then it is preferred to encase the coils 45 of the transition section 39 in a suitable insulation jacket (not shown).

FIG. 5 shows how the catheter can be used by inserting it through the lumen of a guiding catheter 63. Except for a stiffening element 64, the guiding catheter 63 may be of conventional construction and may be a Swan-Ganz thermodilution catheter which is available from American Edwards Laboratories of Irvine, California. The guiding catheter 63, which may have multiple lumens extending longitudinally through a catheter body, may be inserted into the heart through a vein using conventional techniques, and following such insertion, a balloon 65 adjacent the distal end of the guiding catheter is lodged in the pulmonary artery 67. As shown in FIG. 5, the catheter 63 extends through the superior vena cava 66 and is formed into a curve 68 of about 180 degrees as it extends through the right atrium 69 and the right ventricle 71. The guiding catheter 63 has a port 72 leading from one of its lumens into the right ventricle 71.

In the embodiment illustrated, the stiffening element 64 is in the form of an elongated, flexible, resilient wire of metal or plastic bonded into the guiding catheter 63 outside of the lumen with which the port 72 communicates. In the preferred construction illustrated, the stiffening element 64 extends from a location in the right atrium 69 proximally of the port 72 continuously to a location in the right ventricle 71 located distally of the port 72. Thus, regions of the guiding catheter on the opposite sides of the port 72 are stiffened, and such stiffening is controlled to cause the catheter 63 to form the relatively gentle curve 68 in the right heart without kinking as the catheter extends through the right heart to the pulmonary artery 67.

With the guiding catheter 63 positioned in the right heart as shown in FIG. 5, the catheter 11 can be inserted through a lumen of the guiding catheter 63 and out the port 72. As the catheter 11 continues its advancing movement, the electrode 62 contacts a wall 73 of the right ventricle and bends over or deflects along the wall due to the resilience of the distal section 41 all the way to the distal end 48. This causes the electrode 62 and the transition section 39 to resiliently flex and causes the electrode to lie against the wall 73 without penetrating the wall. A circuit can then be completed from the electrode 62 through the heart wall 73 and body fluids in the heart to the electrode 35. The flexibility of the catheter 11, and in particular, of the conductors 17 and 25 at, and distally of the distal electrode 35, maintains the distal electrode 62 in continuous engagement with the wall 73. Of course, the catheter 11 can be inserted directly through an artery or vein into the heart without using the guiding catheter 63. The catheter 11 is flexible throughout its length. However, the resilience and flexibility of the catheter are carefully controlled primarily at the sections 39 and 41 to provide insufficient column strength to penetrate the heart wall 73 and sufficient resilience to maintain contact between the distal electrode 62 and with the heart wall.

FIG. 3b shows a catheter 11a which is identical in all respects not shown or described herein to the catheter 11. Portions of the catheter 11a corresponding to portions of the catheter 11 are designated by corresponding reference numerals followed by the letter "a."

The only difference between the catheters 11 and 11a is that the inner conductor 17a of the catheter 11a is provided in two parts, i.e., a straight segment 75 and a coiled segment 77 appropriately joined together as by solder or welding. For this purpose, the distal end of the straight segment 75 is inserted within a few of the proximal coils of the coiled segment 77. The straight segment 75 defines the first section 37a and the coiled segment 77 defines the transition section 39a and the distal section 41a, i.e., the electrode 62a.

FIG. 3c shows a catheter 11b which is identical to the catheter 11 in all respects not shown or described herein. Portions of the catheter 11b corresponding to portions of the catheter 11 are designated by corresponding reference numerals followed by the letter "b."

In the catheter 11b, the inner conductor 17b comprises a segment 79 and a body 81 of soft, flexible, resilient, conductive elastomeric material attached to the distal end of the segment 79. The segment 79 may be a wire or cable. The distal portion of the segment 79 projects beyond the insulation 43b and terminates in a head 83 of enlarged cross-sectional area.

The segment 79 between the body 81 and the electrode 35b is encased in a jacket 85 of soft, flexible, resilient plastic material, which is a nonconductor. This portion of the segment 79 and the jacket 85 form a transition section 39b of a stiffness intermediate the stiffness of the body 81 and the region of the catheter 11b proximally of such portion of the segment 79. The segment 79 projects only a short distance into the body 81, and hence, the body 81 is the most flexible part of the inner conductor 17b. The jacket 85 may extend into the coils defining the electrode 35b.

The body 81 of elastomeric material may be, for example, molded around the distal tip of the segment 79 so that the head 83 is embedded within the body 81. This tightly retains the body 81 of elastomeric material against the distal end of the jacket 85. If desired, the body 81 may be adhered or bonded to the jacket 85. The body 81 forms the distal electrode 62b. The catheters 11a and 11b may be used in the same manner described above for the catheter 11.

FIG. 4 shows a unipolar catheter 11c which is identical in all respects not shown or described herein to the bipolar catheter 11. The only difference between the catheters 11 and 11c is that the outer conductor 25 is replaced with a flexible tube 87 of a suitable biocompatible plastic material. Portions of the catheter 11c corresponding to portions of the catheter 11 are designated by corresponding reference numerals followed by the letter "c." As shown schematically in FIG. 4, with the unipolar catheter 11c, the circuit is completed through the heart wall 73 to ground, and to accomplish this, the patient is appropriately grounded.

Although exemplary embodiments of the invention have been shown and described, many changes, modifications and substitutions may be made by one having ordinary skill in the art without necessarily departing from the spirit and scope of this invention.

We claim:

1. A flexible tip pacing catheter adapted for insertion into the heart for electrically stimulating the heart comprising:

an elongated body having an elongated passage therein;

an elongated wire conductor;

means for fixing the elongated wire conductor to said elongated body with the conductor being partially in said passage, a first section of said wire conductor lying at least partially within said passage of said body and being straight, said elongated wire conductor having a distal end portion outside of said passage which is flexible and resilient along its length, said catheter having a distal end and an outer periphery, said distal end portion terminating substantially at the distal end of the catheter;

said flexible resilient distal end portion including a flexible electrode outside said body and exposed at the outer periphery of the catheter whereby current can be passed between said electrode and the heart;

said distal end portion of said wire conductor having a distal section closely adjacent the distal end of the catheter which is more flexible than a location on the distal end portion which is spaced proximally from the distal section; and a region of said wire conductor being wound into a coil to form said distal section, said location and at least a part of said flexible electrode.

2. A catheter as defined in claim 1 wherein said coil forms said distal end portion of said conductor.

3. A catheter as defined in claim 1 wherein said coil forms a transition section coupling said first section to said distal section, said distal section is more flexible than said transition section, and said transition section is more flexible than said first section.

4. A catheter as defined in claim 3 wherein the wire of said first section has a greater cross-sectional area than the wire of said transition section and the wire of said transition section has a larger cross-sectional area than the wire of said distal section.

5. A catheter as defined in claim 4 wherein at least a region of the wire conductor of said transition section is of progressively reducing cross-sectional area as such region extends distally.

6. A catheter as defined in claim 3 wherein the turns of the coil of the transition section are spaced greater axially than the turns of the coil of the distal section.

7. A catheter as defined in claim 6 wherein at least a region of the wire conductor of said transition section is of progressively reducing cross-sectional area as such region extends distally.

8. A catheter as defined in claim 1 wherein said body includes a conductive wire having a plurality of coils with a region of said coils being exposed to define a proximal electrode which lies proximally of said location.

9. A catheter as defined in claim 8 wherein the coils adjacent the distal end of said wire of said body are spaced apart axially and said catheter includes an elastomer between said spaced coils.

10. A catheter as defined in claim 1 wherein said catheter includes an elastomer within at least a portion of said coil.

11. A catheter as defined in claim 1 wherein said flexible resilient electrode extends to the distal end of the catheter.

12. A catheter as defined in claim 1 including a proximal electrode spaced proximally of the flexible electrode and said location is between said electrodes.

13. A flexible tip pacing catheter adapted for insertion into the heart for electrically stimulating the heart comprising:

an elongated body having an elongated passage therein;

an elongated wire conductor;

means for fixing said elongated wire conductor to said elongated body with the conductor being partially in said passage, a first section of said wire conductor lying at least partially within said passage of said body and being straight, said elongated wire conductor having a distal end portion outside of said passage which is flexible and resilient along its length, said catheter having a distal end and an outer periphery, said distal end portion terminating substantially at the distal end of the catheter;

said flexible resilient distal end portion including a flexible electrode outside said body and exposed at the outer periphery of the catheter whereby current can be passed between said electrode and the heart;

said distal end portion of said wire conductor having a flexible region located adjacent to and proximally of the flexible electrode with the flexibility of such region tapering as such region extends proximally; and a length of said wire conductor being wound into a coil to form said flexible region and at least a part of said flexible electrode.

14. A catheter as defined in claim 13 wherein the axial spacing between the turns of said coil at said flexible region increases as said flexible region extends proximally.

15. A catheter as defined in claim 13 wherein said wire is of progressively increasing cross-sectional area as the wire extends proximally in said flexible region.

16. A catheter as defined in claim 13 wherein said pacing catheter includes a proximal electrode spaced proximally from said flexible electrode and said region is between said electrodes.

17. A flexible tip pacing catheter adapted for insertion into the heart for electrically stimulating the heart comprising:

an elongated body having an elongated passage therein;

an elongated conductor;

means for fixing the elongated conductor to said elongated body with the conductor being partially in said passage, said elongated conductor having a distal end portion outside of said passage which is flexible and resilient along its length, said distal end portion terminating substantially at a distal end of the catheter;

said flexible resilient distal end portion including a flexible electrode outside said body and exposed at the outer periphery of the catheter whereby current can be passed between said electrode and the heart;

said pacing catheter including a proximal electrode spaced proximally from said flexible electrode; and said pacing catheter having a flexible region between said electrodes with said region being more flexible adjacent the flexible electrode than adjacent the proximal electrode.

18. A catheter as defined in claim 17 wherein the flexibility of said flexible region progressively decreases as such region extends proximally.

19. A catheter as defined in claim 17 wherein said conductor is wound into a coil to form said flexible region and at least a part of said flexible electrode.

20. A catheter as defined in claim 19 wherein the axial spacing between the turns of said coil at said flexible region increases as said flexible region extends proximally.

21. A catheter as defined in claim 19 wherein the conductor is of progressively increasing cross-sectional area as the conductor extends proximally in said flexible region.

22. A catheter as defined in claim 17 wherein said body includes a conductive wire having a plurality of coils with a region of said coils being exposed to define said proximal electrode.

23. A catheter as defined in claim 19 wherein said body includes a conductive wire having a plurality of coils with a region of said coils being exposed to define said proximal electrode, at least some of said coils of said conductive wire are spaced apart and said catheter includes a nonconductive elastomer filling at least some of the coils of the flexible region and the region between the spaced apart coils.

24. A catheter as defined in claim 19 including a nonconductive elastomer extending between said electrodes.

* * * * *